United States Patent [19]
Randolph et al.

[11] Patent Number: 5,619,763
[45] Date of Patent: Apr. 15, 1997

[54] PATIENT HANDLING SYSTEM FOR DIAGNOSTIC IMAGING APPLICATION

[75] Inventors: Alan Randolph, Park Ridge; Herb F. Velazquez, Lombard, both of Ill.

[73] Assignee: Siemens Medical Systems, Inc., Iselin, N.J.

[21] Appl. No.: 409,785

[22] Filed: Mar. 24, 1995

[51] Int. Cl.$^6$ ........................................ A61B 6/02
[52] U.S. Cl. ........................ 5/601; 5/623; 378/209
[58] Field of Search ............................. 378/209; 5/601, 5/611, 621, 623, 86.1, 662

[56] References Cited

U.S. PATENT DOCUMENTS

| 3,840,221 | 10/1974 | Hogan | 5/623 |
|---|---|---|---|
| 4,034,224 | 7/1977 | Heavens et al. | 250/439 |
| 4,088,888 | 5/1978 | Brook et al. | 250/445 |

FOREIGN PATENT DOCUMENTS

| 3222332C2 | 12/1983 | Germany. |
|---|---|---|
| 3339781A1 | 5/1985 | Germany. |

*Primary Examiner*—Michael F. Trettel
*Attorney, Agent, or Firm*—Mark H. Jay

[57] ABSTRACT

A patient pallet has two sides, a proximal end and a distal end. The patient pallet is horizontally elongated and is positioned to support a human patient with the patient's body axis horizontal. The pallet is supported by a pedestal. The pedestal is vertically moveable so that the patient may be raised and lowered with respect to the floor. The pedestal receives the patient pallet so that the pallet can slide horizontally, parallel to the floor. A pallet support is horizontally spaced from the pedestal and is so located that the distal end of the patient pallet can be supported by the pallet support when the patient pallet is slid horizontally. In this way, the patient pallet is either supported by the pedestal alone or by the pedestal and the pallet support. In the latter instance, the patient pallet bridges between the pedestal and pallet support. Left and right horizontally elongated arm rests are provided. Each of these is individually securable to a corresponding one of the sides of the patient pallet and slides together with it when so secured. When a particular study makes it necessary or convenient to provide support for one or two arms, either one or both of the arm supports are secured to the patient pallet and move together with it. If no arm support is necessary or appropriate, the patient pallet slides by itself.

7 Claims, 7 Drawing Sheets

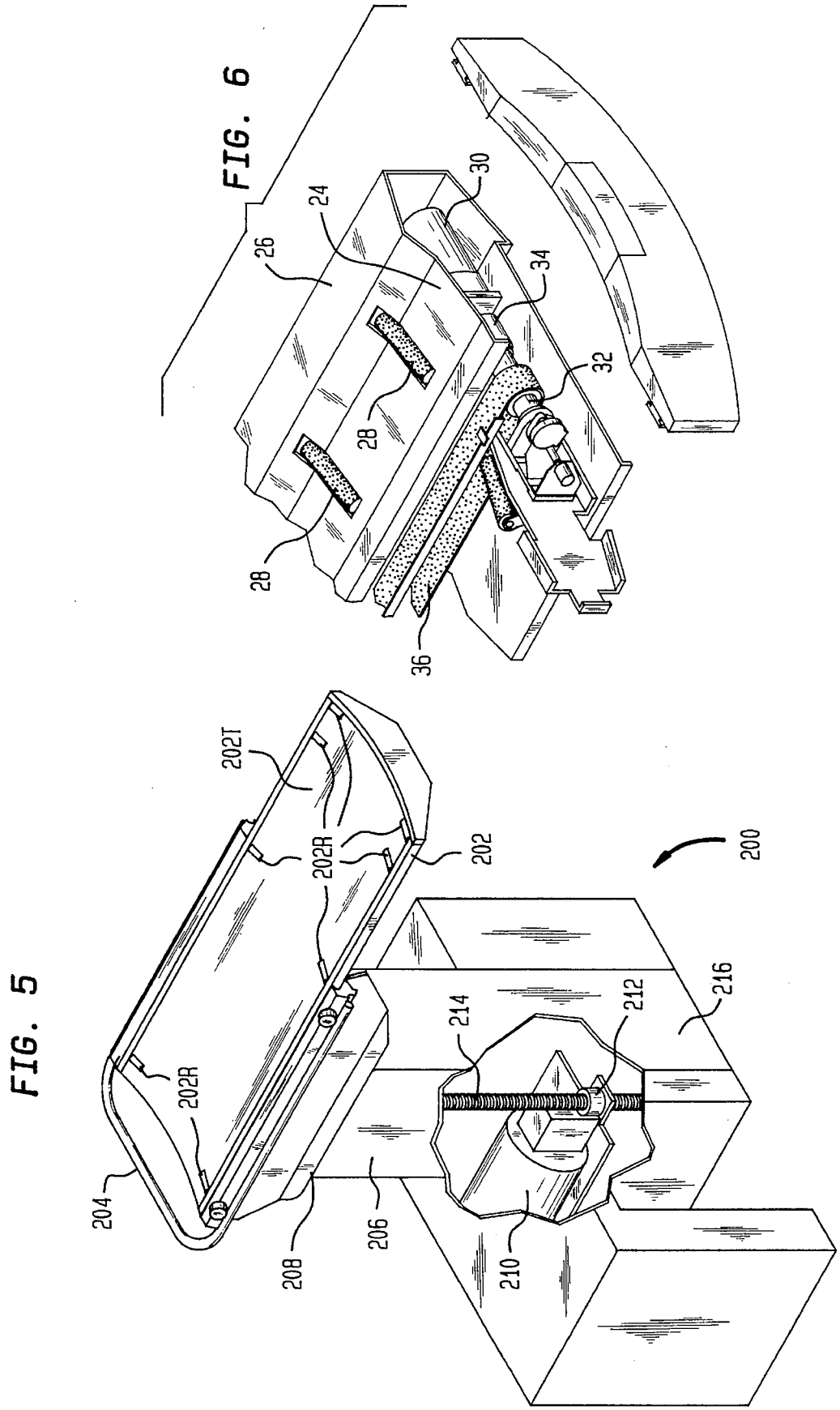

PATIENT HANDLING SYSTEM FOR DIAGNOSTIC IMAGING APPLICATION

BACKGROUND OF THE INVENTION

The invention relates to diagnostic imaging equipment, and more particularly relates to those parts of diagnostic imaging equipment which support the patient while the patient is undergoing an imaging study. In its most immediate sense, the invention relates to a patient handling system for use with nuclear medicine imaging equipment.

In nuclear medicine diagnostic imaging, a radioisotope is administered to the patient. The radioisotope is chosen to be taken up by an organ or structure of interest (e.g. the heart or the patient's skeleton). The patient is then placed adjacent one or more detectors. As the radioisotope emits gamma radiation, the radiation is detected by the detector(s) and used to form images of the organ or structure of interest.

In some nuclear medicine studies, the patient sits on e.g. a chair and placed e.g. so that his chest is adjacent a detector or so his torso is located between two detectors. In other studies, the patient lies horizontally while the detector(s) rotate about the patient's body axis. In still other studies, the patient lies horizontally while the detector(s) move horizontally parallel to the patient's body axis. The variety of patient positions used in nuclear medicine studies makes it advantageous to provide a patient handling system which is sufficiently versatile to make it easy to carry out many different types of nuclear medicine studies.

Additionally, when a patient lies horizontally, the way in which the patient must be supported depends upon the study which is to be conducted. In a typical whole body study, the patient lies supine with his or her arms at the sides and is most comfortably supported when both arms are supported by arm rests. For e.g. a cardiac SPECT study, wherein the patient lies supine with one or both arms above the head, either one arm or neither arm is supported on an arm rest. For a conventional 360° SPECT study, both the patient's arms should be raised over the head. It would be advantageous to provide a patient handling system wherein various arm support options are available and wherein arm support could easily be provided and removed based upon the clinical requirements of the studies to be carried out.

Furthermore, for certain studies (e.g. planar whole body bone scans) the patient must be positioned so as to lie completely within the field of view of the detector(s). Because the sensitive crystal surface (and thus the field of view) of the detector(s) is smaller than the housing of the detector(s), and because the patient is frequently positioned at a location which is remote from the detector(s), it is sometimes difficult to determine whether the patient is properly positioned relative to the field(s) of view.

One object of the invention is to provide a patient handling system which is sufficiently versatile so as to make it easy to carry out many different types of nuclear medicine studies.

Another object is to provide such a system which makes it easy to provide or eliminate arm support depending upon the particular study being conducted.

Another object is, in general, to improve on known patient handling systems for use with diagnostic imaging equipment.

In accordance with the invention, there is provided a patient pallet having two sides, a proximal end and a distal end. The patient pallet is horizontally elongated and is positioned to support a human patient with the patient's body axis horizontal. In further accordance with the invention, the pallet is supported by a pedestal. The pedestal is vertically moveable so that the patient may be raised and lowered with respect to the floor. The pedestal receives the patient pallet so that the pallet can move lengthwise, parallel to the floor. As a result, the patient pallet is always supported at and adjacent its proximal end by the pedestal.

A pallet support is also provided in accordance with the invention. The pallet support is horizontally spaced from the pedestal and is so located that the distal end of the patient pallet can be supported by the pallet support when the patient pallet is moved lengthwise. In this way, the patient pallet is either supported by the pedestal alone or by the pedestal and the pallet support. In the latter instance, the patient pallet bridges between the pedestal and pallet support.

In further accordance with the invention, left and right horizontally elongated arm rests are provided. Each of these is individually securable to a corresponding one of the sides of the patient pallet and slides together with it when so secured. Thus, when a particular study makes it necessary or convenient to provide support for one or two arms, either one or both of the arm supports are secured to the patient pallet and move together with it. If no arm support is necessary or appropriate, the patient pallet moves by itself.

Advantageously, and in accordance with the preferred embodiment of the invention, indicating means are attached to each of the arm rests and move together with them. The indicating means indicate side boundaries beyond which the patient's body should not project. By properly positioning the patient with reference to the indicating means, the patient is always located within the field of view of the camera detector(s).

Advantageously, and in accordance with the preferred embodiment, the indicating means comprises two elongated flaps, each one extending parallel and adjacent to a corresponding one of the sides of the patient pallet. Each flap has a raised position in which it extends upwardly from the patient pallet and a lowered position in which it lies flat upon the patient pallet. When the patient is to be placed upon the patient pallet (e.g. by transfer from a patient gurney), the flaps lie flat so as not to present an impediment. Once a study is to be commenced, the flaps can be raised to make sure that the patient's body is not located outside the field of view of the detectors.

Further advantageously, and in accordance with the preferred embodiment of the invention, the pedestal can be moved around on the floor. This permits the pedestal and patient pallet to be moved out of the way so that the patient can be imaged while e.g. sitting upon a chair. Likewise advantageously, and in accordance with the preferred embodiment, the pedestal and the pallet support are connected together and the pallet support is raised and lowered to correspond to vertical movement of the pedestal and patient pallet. This makes it easy to slide the patient pallet horizontally so that its distal end rests upon the pallet support.

BRIEF DESCRIPTION OF THE DRAWINGS

The invention will be better understood with reference to the following illustrative and non-limiting drawings, in which:

FIG. 5 is a view of the pallet support showing certain construction details;

FIG. 6 is a view showing certain construction details of the pedestal;

DETAILED DESCRIPTION OF PREFERRED EMBODIMENTS

Figure 1:
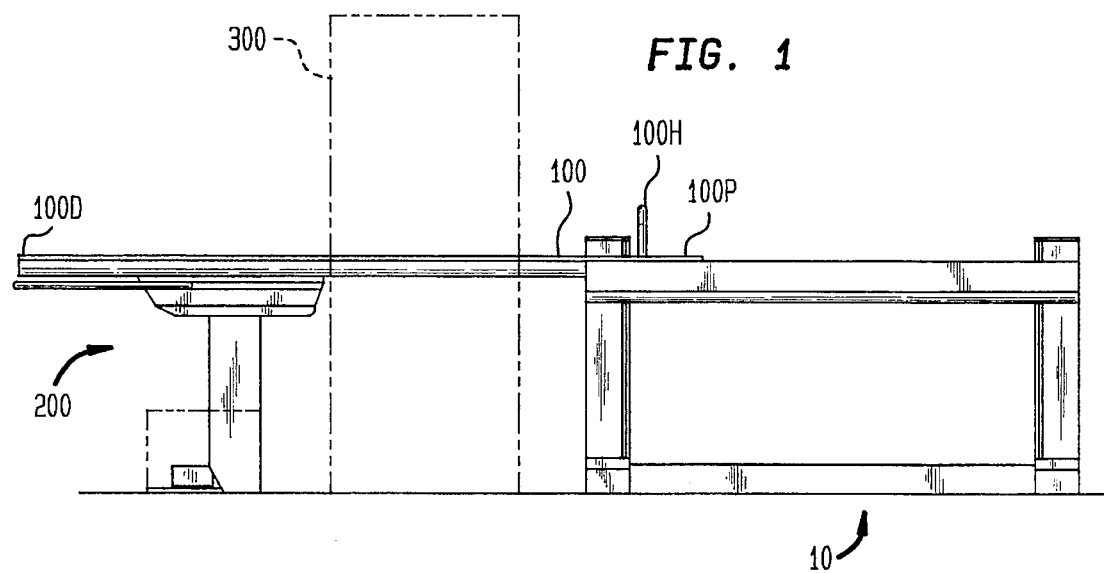
FIG. 1 is a side schematic views of the preferred embodiment of the invention, showing the relationship of the preferred embodiment to the gantry of a scintillation camera.
Figure 2A:
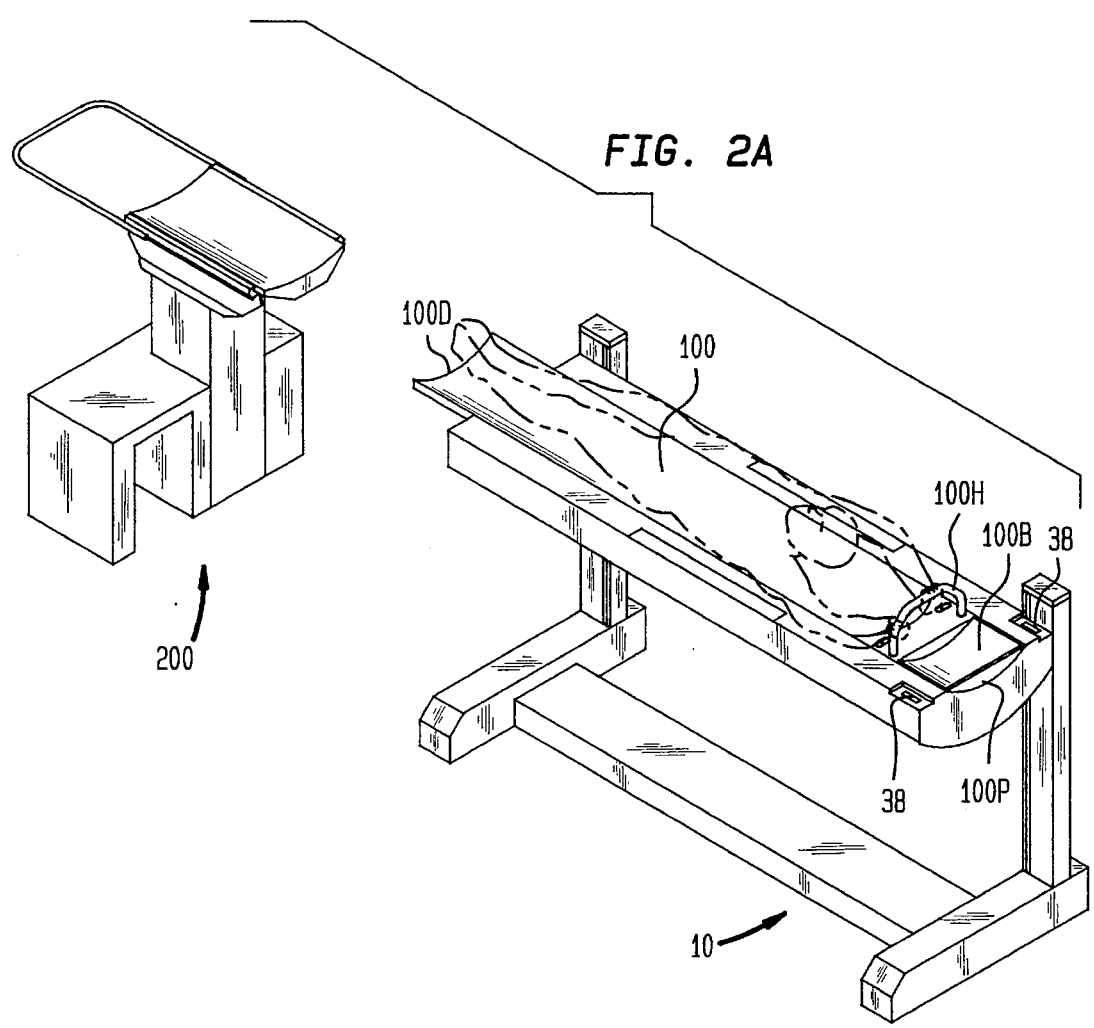
FIGS. 2A and 2B schematically illustrate the patient pallet in, respectively, its fully retracted and advanced states.

At the most general level (see FIG. 1), the preferred embodiment of the invention has three main structures: a pedestal 10, a patient pallet 100 and related parts, and a pallet support 200 which is spaced from the pedestal 10. When the patient (see FIG. 2A) is to be supported in a horizontal position, the patient is placed on the pallet 100 and the pallet 100 (together with other structure described in more detail below) can be horizontally moved toward the pallet support 200. The patient is thereby inserted feet first into the gantry (not specifically shown, but located in region 300) of a scintillation camera system. In certain instances, the pallet 100 will hang off the pedestal 10 with its distal end 100D unsupported; in other instances, the distal end 100D of the pallet will be supported by the pallet support 200. Alternatively, the pedestal 10 can be rolled away from the gantry and a study can be carried out with the patient sitting on a chair adjacent the gantry in region 300.

The description below will commence with a description of the pedestal 10, the pallet 100 and the associated structure. Thereafter, the operation of the pedestal 10 and the pallet support 200 will be explained. Finally, the control system used in the preferred embodiment will be described.

An elongated pedestal generally indicated (FIG. 2B) by reference number 10 has a lower frame 2 and an upper frame 4. The lower frame 2 and the upper frame 4 are connected together by vertically elongated lift mechanisms 6 which permit the upper frame 4 to be raised and lowered with respect to the lower frame 2. As can best be seen in FIG. 3, the upper frame 4 is supported on two supports 8. Each of the supports 8 is threaded upon a corresponding acme screw 12 and the acme screws 12 are connected together by a belt drive 14 which is driven by a drive motor 16. Rotation of the drive motor 16 raises or lowers the upper frame 4 by rotating the acme screws 12; the direction of rotation of the drive motor 16 determines whether the upper frame 4 is raised or lowered.

Figure 2B:
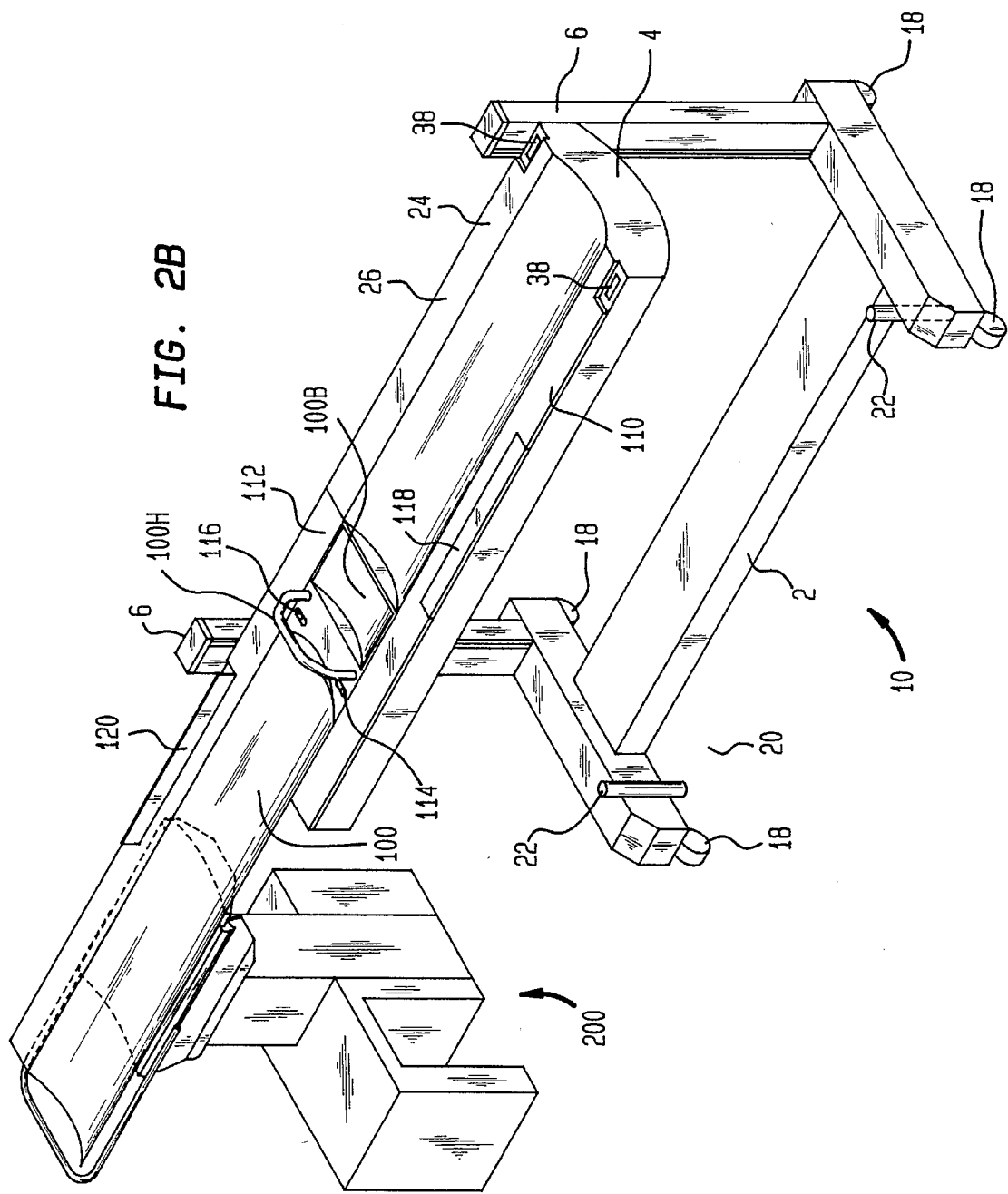
Figure 3:
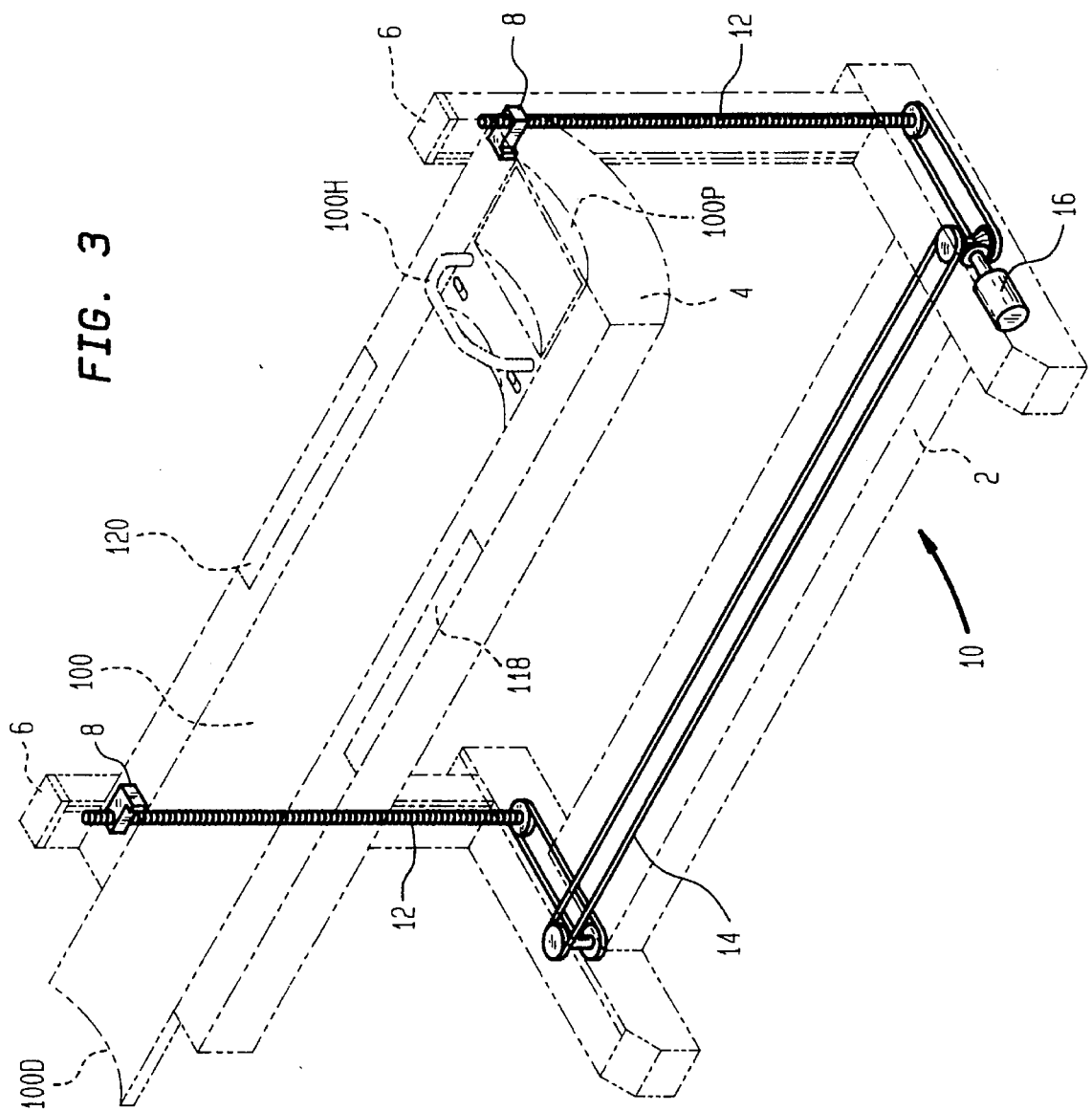
FIG. 3 is a view of the pedestal showing certain construction details.

Referring to FIG. 2B, four rollers 18 (which may for example be casters or wheels) are secured to the lower frame 2 to allow the pedestal 10 to be rolled on the floor 20. When the pedestal 10 is to be located in proper position with respect to the gantry at region 300, locating pins 22 on the lower frame 2 are inserted into mating recesses (not shown) in the floor 20; when the pedestal 10 is to be moved, the pins 22 are lifted out of the recesses.

The upper frame 4 has a central region 24 (FIG. 2B) which is elongated and which is curved to face concave upward. The upper frame 4 also has two elongated side surfaces 26 which are adjacent the sides of the central region 24 and which extend transversely outwardly therefrom.

A curved patient pallet 100 is supported by, and rolls on, rollers 28 which project upwardly through openings in the central region 24. The patient pallet 100 faces concave upwardly (to receive a patient lying upon it). The patient pallet 100 is elongated, and has a proximal end 100P and a distal end 100D. The patient pallet 100 is moveable lengthwise back and forth with respect to the central region 24. Normally, this motion is brought about by operation of a drive motor 30 (FIG. 6). The drive motor 30 is connected to a pully 32 via an electrically operable clutch 34, and the pully 32 drives a belt 36 which is secured to the lower portion of the patient pallet 100.

In an emergency (for example, if a patient has a heart attack or a seizure and must be immediately transferred to e.g. an intensive care unit) the patient pallet 100 must be moved quickly so that the patient can be quickly removed. The preferred embodiment accommodates this contingency by making it possible for the patient pallet 100 to be moved manually. To do this, pushbuttons 38 are provided at the end of the upper frame 4. These pushbuttons 38 are operatively connected to the clutch 34, and when either one or both of the pushbuttons 38 are operated the clutch 34 is disengaged and the belt 36 and pully 32 are free to rotate without rotating the shaft of the drive motor 30. The pallet 100 can then be moved manually by pushing on a handle 100H which is secured to the top of the pallet 100 forwardly of the proximal end 100P. Advantageously, the pallet 100 is made of aluminum, but this is not required; it is only necessary that the pallet 100 be sufficiently rigid to support heavy patients and that it be minimally opaque to gamma radiation.

Figure 7:
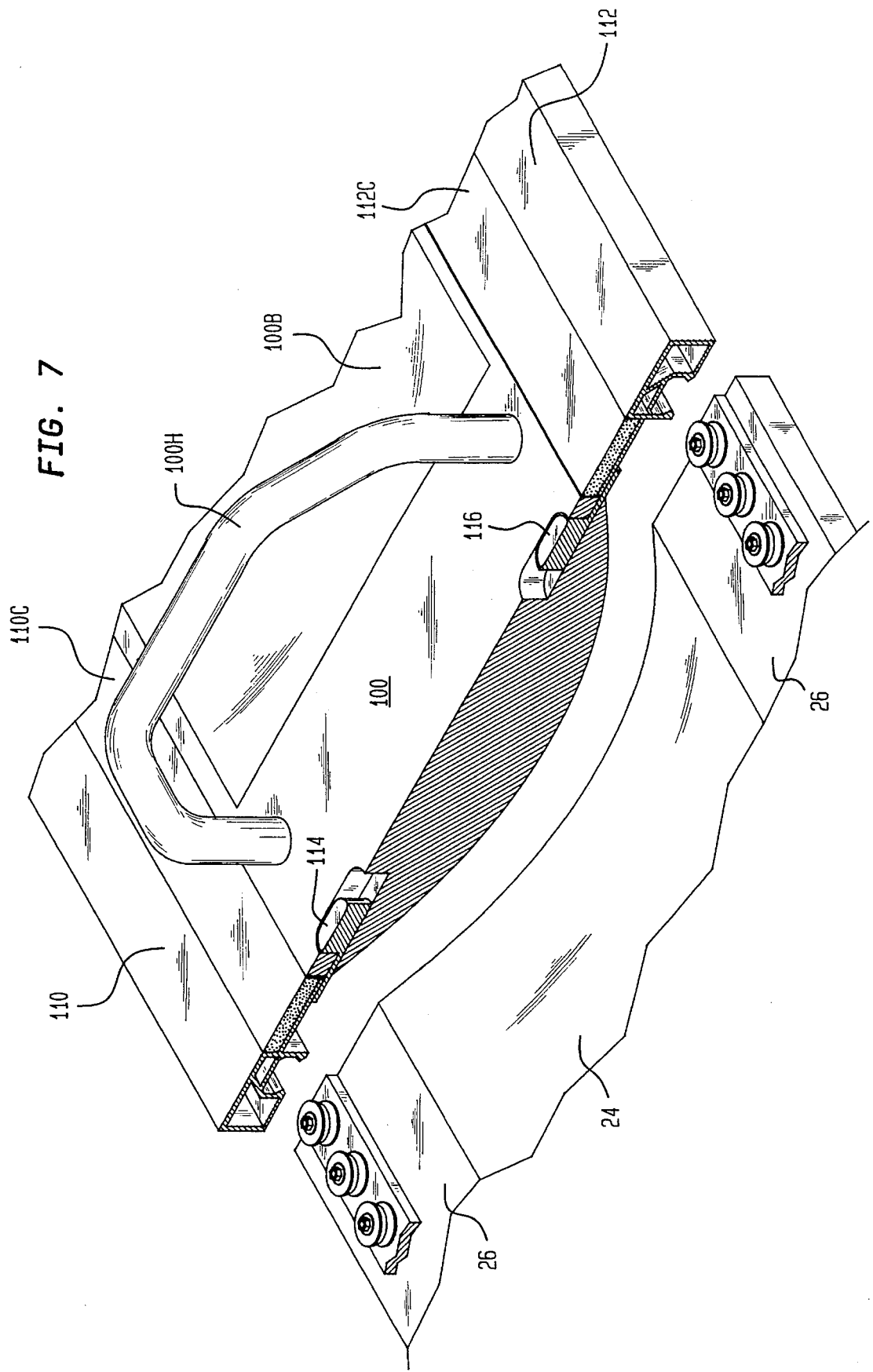
FIG. 7 is a view showing certain construction details of the engagement between the arm supports and the pedestal assembly.
Figure 8:
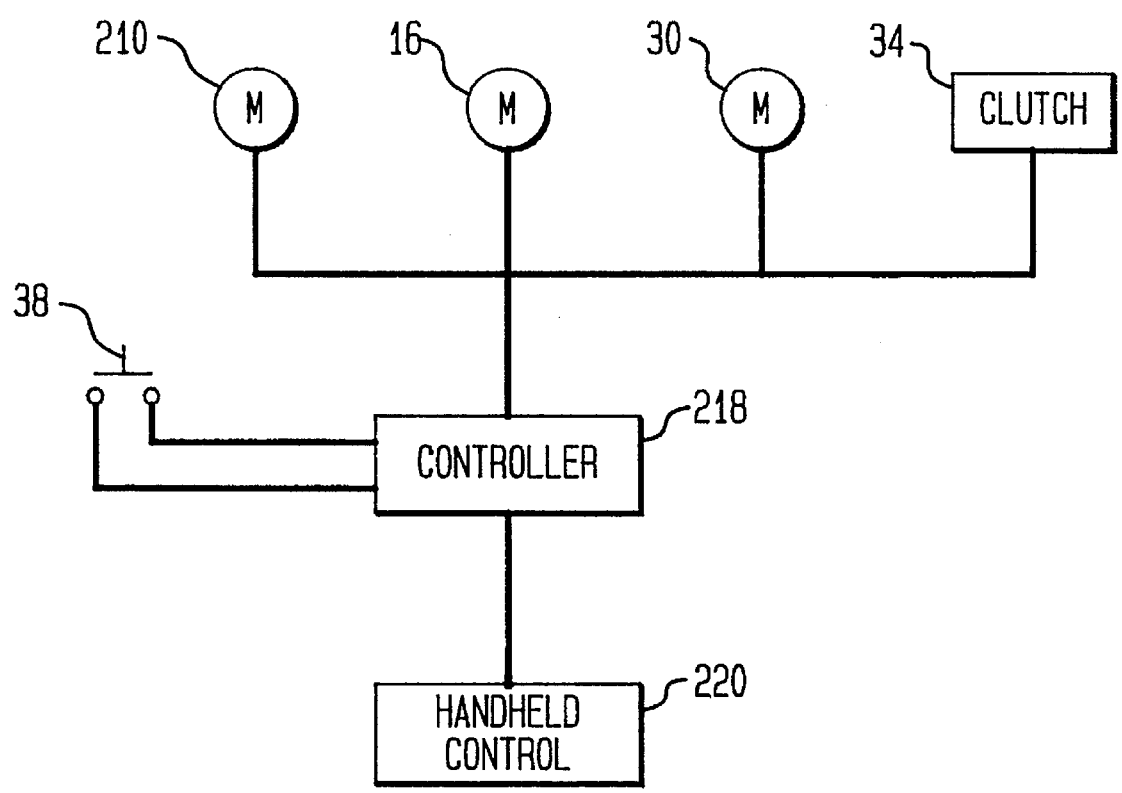
FIG. 8 is a block diagram showing the control system used in accordance with the preferred embodiment of the invention.

Elongated arm supports 110 and 112 slide upon the side surfaces 26. The arm supports 110 and 112 may be individually locked to the pallet 100 by slides 114 and 116 respectively. Slide 114, when engaged with a corresponding recess in the arm support 110, causes the arm support 110 to slide lengthwise along the surface 26 when the pallet 100 is moved lengthwise with respect to the central region 24. Likewise, slide 116, when engaged with a corresponding recess in the arm support 112, causes the arm support 112 to slide lengthwise along the surface 26 when the pallet 100 is slid along the central region 24. In this way, the technician is provided with the option of using two arm supports, one arm support or no arm supports, depending upon the requirements of a particular study and the preferences of the patient. For patient comfort, the arm supports 110 and 112 may be provided with cushions 110C and 112C respectively (see FIG. 7), the cushions 110C and 112C being immediately adjacent the patient pallet 100.

The fields of view of the detectors (not shown) of the scintillation camera system are narrower than the total transverse width of the pedestal 10 (i.e. the distance between the outer transverse edges of the arm supports 110 and 112). For certain studies, the patient's arms (not shown) should always lie within such fields of view. To prevent the patient's arms from extending too far sideways, the preferred embodiment of the invention provides indicators which show the outermost boundaries beyond which the patient's arms should not project. These indicators will now be described.

Figure 4A:
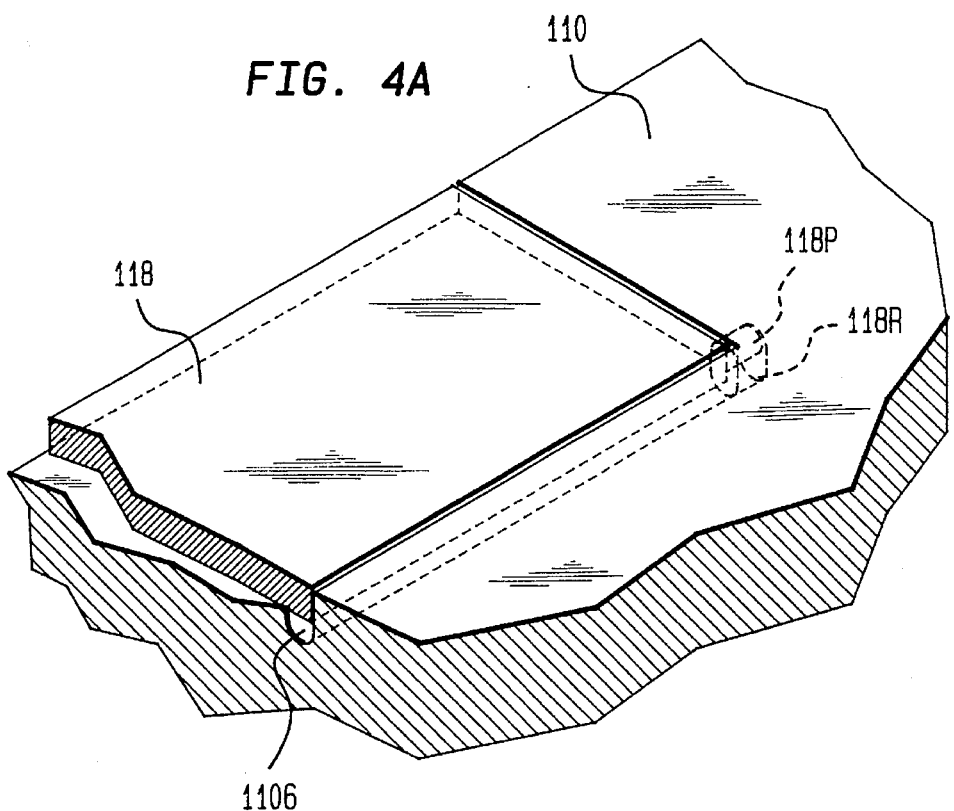
FIGS. 4A and 4B show one end of one of the flaps in lowered and raised positions respectively.
Figure 4B:
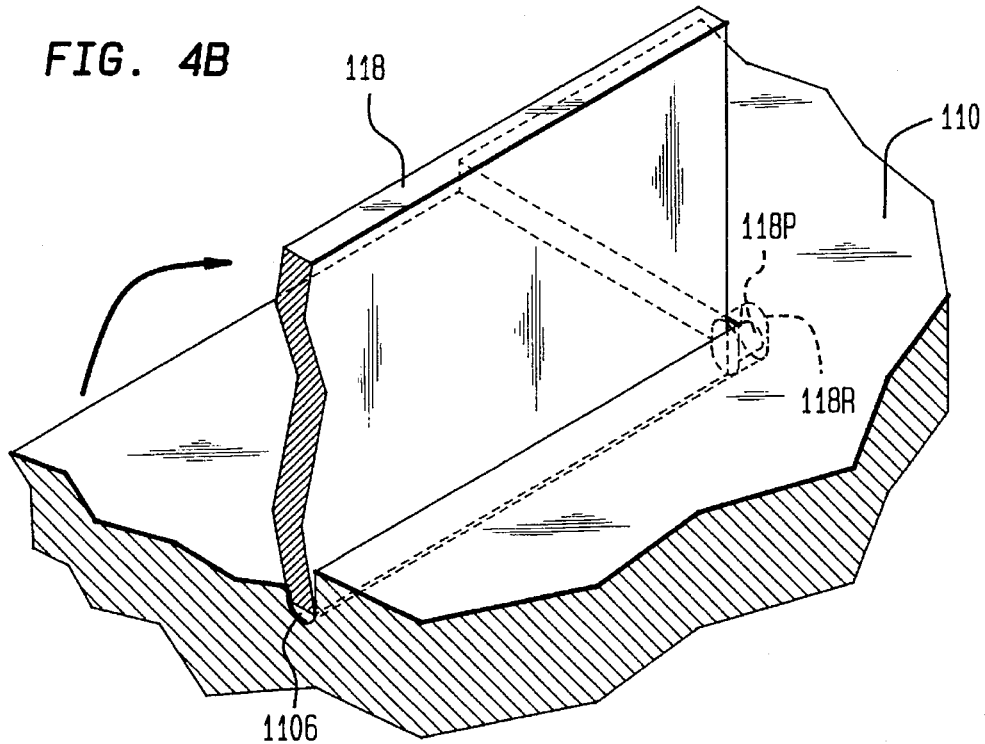

Each of two like flaps 118 and 120 is pivotally secured to a corresponding one of the arm supports 110 and 112 (see FIG. 2B). In each case, this is accomplished by pairs of pins which are mounted to the ends of the flaps 118 and 120; a pins 118P for one end of the flap 118 is shown in FIGS. 4A and 4B. The pins engage recesses in the arm supports 110 and 112; a recess 118R for the pin 118P is shown in FIGS. 4A and 4B.

Elongated grooves are located in the top surfaces of the arm supports 110 and 112. The groove 110G for the arm support 110 is shown in FIGS. 4A and 4B. Each groove (e.g. groove 110G) is slightly wider than the thicknesses of the corresponding flap (e.g. flap 118). When the flaps 118 and 120 are to be raised to show the proper boundaries beyond which the patient's arms should not project, the flaps 118 and 120 are lifted and rotated so as to rest within the grooves (e.g. groove 110G). The flaps 118 and 120 then project upwardly, perpendicular to the arm supports 110 and 112. When the patient has been properly positioned, the flaps 118 and 120 may be lifted out of the grooves (e.g. groove 110G) and folded down, flush upon the arm supports 110 and 112.

To summarize, let it be assumed that a patient is to be placed upon the pallet 100 and is to undergo an imaging study. Initially, the pallet 100 will be fully retracted onto the pedestal 10, the arm supports 110 and 112 will likewise be fully withdrawn, and the flaps 118 and 120 will be folded flush upon the arm supports 110 and 112. The patient is transferred to the pallet 100 and placed in the appropriate position (prone, supine, on the side) on it. Then, the technician determines whether patient comfort or other considerations require the use of either one or both of the arm supports 110 and 112. If, e.g., the study is to be a whole body bone scan, both arm supports 110 and 112 will be required and the slides 114 and 116 will be moved outwardly so that the arm supports 110 and 112 are locked to the pallet 100. If, e.g. the study does not require the use of any arm supports, the slides 114 and 116 will remain at their innermost positions so the pallet 100 is not linked to the arm supports 110 and 112.

Let it be assumed that the study is to be a whole body bone scan. In this case, the patient's arms should lie within predetermined boundaries so that the arm bones will be within the field(s) of view of the detector(s). To verify that the patient is properly positioned, the flaps 118 and 120 are inserted in the corresponding grooves (e.g. groove 110G) so they project upwardly from the arm supports 110 and 112. The flaps 118 and 120 then show the maximum lateral displacement of the patient's arms, and the technician can make sure that the arms lie within the boundaries established by the flaps 118 and 120.

Then, the technician operates the system to cause the pallet 100 to be moved toward the gantry in the region 300. Because the study is a whole body bone scan, both arm supports 110 and 112 are locked to the pallet 100 and the patient's arms can rest upon them during the study. Thereafter, the pallet 100 is moved back and the arm supports 110 and 112 are carried backwards as well.

The pallet support 200 will now be described with reference to FIG. 5. The pallet support 200 has a top 202, a shield bar 204 and a main support 206. The top 202 is supported by the main support 206 at a pivot 208, and the shield bar 204 is slidibly secured to the top 202 so that it can be pulled out (see e.g. FIGS. 2A and 2B) or pushed in (see FIG. 5).

The top 202 serves to support the distal end 100D of the patient pallet 100 when the patient pallet 100 is extended sufficiently far from the pedestal 10. Rollers 202R on the top surface 202T of the top 202 serve to make it easy to move the patient pallet 100 across the top surface 202T. Because in use the distal end 100D of the patient pallet 100 may not merely lie on the top 202 but indeed may project past it (see FIG. 2B), in accordance with the preferred embodiment the shield bar 204 is provided to delimit a region where the patient pallet 100 may go (and where e.g. hospital staff should refrain from going). When the invention is not in use and the patient pallet 100 is fully withdrawn onto the pedestal 10, the shield bar 204 may be pushed in towards the top 202 so that personnel are not prevented from e.g. walking between the patient support 200 and a closely adjacent wall. While the use of a slidable shield bar 204 is preferred for this reason, the shield bar 204 need not be slidable and may be fixed in place. The pivot 208 is provided so the top 202 can be pivoted counterclockwise as viewed in FIG. 1. This prevents the top 202 from projecting into the gantry at 300, making it possible to e.g. move the pedestal 10 out of the way and to insert a patient's head into the gantry at 300 while the patient is resting upon a stretcher which has been wheeled up to the gantry.

As stated above, in certain instances, the pallet 100 is moved sufficiently far so that the distal end 100D of the pallet 100 rests upon the pallet support 200. To make this easy to do, the pallet support 200 is also equipped with a mechanism which causes the pallet support 200 to be raised and lowered with respect to the floor 20. In the preferred embodiment, the mechanism includes a drive motor 210 which drives a gear 212. The gear 212 engages an acme screw 214. The motor 210 is fixed with respect to a base 216 which in turn is fixed to the floor 20. The acme screw 214 is secured to a movable pedestal (not shown) which supports the pallet support 200. Thus, when the drive motor 210 is operated, the pedestal and the pallet support 200 are moved up or down (depending on the direction of rotation of the drive motor 210).

Advantageously, the drive motor 210, the drive motor 30 and the lift mechanisms 8 are connected to, and controlled by, a common controller 218. The controller 218 is in turn is controlled by a handheld control 220. When the drive motor 16 is operated under the control of the handheld control 220, the drive motor 210 is correspondingly operated and the pallet support 200 is raised and lowered as well. This makes it easy for the distal end 100D of the pallet 100 to be rested upon the pallet support 200, since the heights of the pedestal 10 and the pallet support 200 are always matched. Further advantageously, when the patient pallet 100 is to be advanced or retracted with respect to the pedestal 10, this is accomplished by operation of the handheld control 220 as well.

Advantageously, and in accordance with the preferred embodiment, a bin 100B is placed at the proximal end 100P of the patient pallet 100, immediately adjacent the handle 100H. The bin 100B is sufficiently large to receive the handheld control 220 and to make it possible for the control 220 to always be stored in a convenient location when not in use.

Although a preferred embodiment has been described above, the scope of the invention is limited only by the following claims:

We claim:

1. A patient handling system, comprising:

a patient pallet with two sides, a proximal end and a distal end, the patient pallet being horizontally elongated and positioned to support a human patient with the patient's body axis horizontal;

a pedestal supporting the patient pallet, the pedestal being vertically moveable, whereby the patient may be raised and lowered with respect to the floor, and the pedestal receiving the patient pallet in such a manner that the pallet is moveable lengthwise with respect to the pedestal, whereby the patient pallet is always supported at and adjacent its proximal end by the pedestal;

a pallet support, the support being horizontally spaced from the pedestal and being so located that the distal end of the patient pallet can be supported by the pallet support when the patient pallet is moved lengthwise;

left and right horizontally elongated arm rests, each being individually securable to a corresponding one of the sides of the patient pallet and moving together therewith when so secured; and means, attached to each arm rest and moving together therewith, for indicating side boundaries beyond which the patient's body should not project.

2. The system of claim 1, wherein said indicating means comprises two elongated flaps, each one extending parallel and adjacent to a corresponding one of the sides of the patient pallet, each flap having a raised position in which it extends upwardly from the patient pallet and a lowered position in which it lies flat upon the patient pallet.

3. The system of claim 2, wherein the patient pallet has two parallel grooves, each extending parallel and adjacent to one of the sides of the patient pallet, and wherein each flap is dimensioned to fit into its corresponding groove when the flap is in the raised position.

4. The system of claim 1, wherein the patient pallet is curved concave facing upwardly.

5. The system of claim 1, wherein the patient pallet has an open-topped bin located at its proximal end.

6. The system of claim 1, wherein the pedestal is horizontally moveable with respect to the floor.

7. The system of claim 1, wherein the pedestal and the pallet support are connected together, and further including means for causing the pallet support to be raised and lowered to correspond to vertical movement of the pedestal and patient pallet.

* * * * *